United States Patent
Boese et al.

(10) Patent No.: US 8,848,999 B2
(45) Date of Patent: Sep. 30, 2014

(54) METHOD FOR INCREASING UPDATING RATE OF RECONSTRUCTION OF A CURRENT THREE-DIMENSIONAL IMAGE DATASET OF AN OBJECT DURING A MONITORING PROCESS AND X-RAY DEVICE

(75) Inventors: Jan Boese, Eckental (DE); Frank Dennerlein, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 696 days.

(21) Appl. No.: 13/094,423

(22) Filed: Apr. 26, 2011

(65) Prior Publication Data

US 2011/0268341 A1    Nov. 3, 2011

(30) Foreign Application Priority Data

Apr. 30, 2010  (DE) .......................... 10 2010 028 446

(51) Int. Cl.
*G06K 9/00*  (2006.01)
*A61B 6/00*  (2006.01)
*H01J 35/06*  (2006.01)
*G06T 11/00*  (2006.01)
*A61B 19/00*  (2006.01)

(52) U.S. Cl.
CPC ......... *A61B 6/4007* (2013.01); *G06T 2211/412* (2013.01); *A61B 6/4021* (2013.01); *H01J 2235/068* (2013.01); *H01J 2201/30469* (2013.01); *A61B 2019/5242* (2013.01); *H01J 2235/062* (2013.01); *H01J 35/065* (2013.01); *A61B 6/5205* (2013.01); *G06T 11/006* (2013.01)
USPC .......................................................... 382/131

(58) Field of Classification Search
None
See application file for complete search history.

(56) References Cited

U.S. PATENT DOCUMENTS

| | | | | |
|---|---|---|---|---|
| 4,482,958 A * | 11/1984 | Nakayama et al. | ............. | 378/14 |
| 8,014,616 B2 * | 9/2011 | Chakraborty et al. | ........ | 382/233 |
| 2006/0072801 A1 * | 4/2006 | Deman et al. | ................ | 382/131 |
| 2007/0058861 A1 * | 3/2007 | Fujimori | ....................... | 382/167 |
| 2007/0268287 A1 * | 11/2007 | Magnin et al. | ................ | 345/419 |
| 2009/0161820 A1 * | 6/2009 | Raupach | ......................... | 378/19 |
| 2011/0142316 A1 * | 6/2011 | Wang et al. | ................... | 382/131 |
| 2011/0268341 A1 * | 11/2011 | Boese et al. | .................. | 382/132 |
| 2012/0063659 A1 * | 3/2012 | Wang et al. | ................... | 382/131 |
| 2013/0034201 A1 * | 2/2013 | Boese et al. | ...................... | 378/9 |
| 2013/0077847 A1 * | 3/2013 | Hansis et al. | ................ | 382/131 |
| 2013/0308845 A1 * | 11/2013 | Lenox | .......................... | 382/131 |

FOREIGN PATENT DOCUMENTS

| DE | 10 2008 033 150 A1 | 2/2010 |
|---|---|---|
| WO | WO 98/36690 A1 | 8/1998 |

* cited by examiner

*Primary Examiner* — Tahmina Ansari

(57) ABSTRACT

A method for reconstruction of an actual three-dimensional image dataset of an object during a monitoring process is proposed. Two-dimensional X-ray projection images which correspond to a recording geometry are continuously recorded from different projection angles. The three-dimensional image dataset are reconstructed from a first number of these projection images, especially by a back projection method. The proportion of the oldest projection image contained in the current three-dimensional image dataset is removed from the three-dimensional image dataset and the proportion of the actual projection image is inserted in the three-dimensional image dataset after each recording of the actual projection image.

20 Claims, 2 Drawing Sheets

METHOD FOR INCREASING UPDATING RATE OF RECONSTRUCTION OF A CURRENT THREE-DIMENSIONAL IMAGE DATASET OF AN OBJECT DURING A MONITORING PROCESS AND X-RAY DEVICE

CROSS REFERENCE TO RELATED APPLICATIONS

This application claims priority of German application No. 10 2010 028 446.7 filed Apr. 30, 2010, which is incorporated by reference herein in its entirety.

FIELD OF THE INVENTION

The invention relates to a method for reconstruction of a current three-dimensional image data set of an object during a monitoring process. In addition the invention relates to an associated X-ray device.

BACKGROUND OF THE INVENTION

The use of X-ray devices for monitoring processes is known, especially in the imaging of dynamic processes. Their primary use is for monitoring during medical interventions. In these applications a real time capability of the imaging modality is of major importance. In the case of two-dimensional projection radiography such real time imaging is now standard practice. With such two-dimensional monitoring the image refresh rate is principally only determined by the readout speed/frequency of the detector. Despite this, it is precisely in more complex scenarios that a three-dimensional monitoring imaging with a high image refresh rate and short delays is required.

However it is problematic here that for three-dimensional imaging a plurality of two-dimensional X-ray projection images from different directions of view, i.e. from different recording geometries, is needed and that a reconstruction algorithm must first convert this series of 2D projection image into a three-dimensional image dataset. This means however that a three-dimensional image dataset can only be provided after a delay which corresponds to the imaging time and the reconstruction time. Accordingly the 3D refresh rate is far lower than the detector readout frequency. It can thus occur that rapid changes in the object are not registered.

Nowadays it is usual during the imaging of dynamic processes to initially record all projection images necessary for a three-dimensional reconstruction, then undertake a reconstruction for this point in time and subsequently continue with the recording of further projection images.

SUMMARY OF THE INVENTION

The underlying object of the present invention is thus to specify a method for increasing the updating rate of three-dimensional image datasets during monitoring and for minimizing their delay. The method proposes that during the monitoring process two-dimensional X-ray projection images are continuously recorded from different projection angles which correspond to an imaging geometry and the three-dimensional image dataset is reconstructed from a first number of these projection images, especially by a back projection method.

To achieve this object, the invention makes provision in a method for the proportion of the oldest projection image contained in the current three-dimensional image dataset to be removed from the three-dimensional image dataset and the proportion of the current projection image to be inserted.

A method is thus proposed for calculating a dynamic three-dimensional image dataset, with the three-dimensional image dataset, after each recording of a current projection image, being calculated in each case taking into account the last first number of projection images, so that the refresh rate of the three-dimensional image dataset matches the recording frequency of the projection images. The first number can thus be considered as the width of a sliding window which marks the projection images contributing to the current reconstruction. In this way the updating rate of the three-dimensional image datasets is identical to the recording frequency of the individual projection images. This is achieved by only the respective changed image information of the three-dimensional volume being renewed in order to avoid a complex complete reconstruction.

The respective three-dimensional image dataset currently able to be displayed is thus calculated from the first number of projection images last recorded. A three-dimensional image dataset is consequently always changed after the first number of updating steps in a completely independent dataset in each case.

Thus an efficient option in computing terms is described for generating a three-dimensional representation of a dynamic object which is renewed in a frequency which corresponds to the readout frequency of the detector. The renewal of the three-dimensional image dataset does not require complete reconstruction in this case but only an update which comprises the current projection image and a previously recorded projection image. A three-dimensional reconstruction in real-time can thus be achieved without any great hardware outlay.

In such cases there is provision in the usual monitoring methods as will be noted below, for the three-dimensional image dataset or a representation derived therefrom to be shown after each updating always in the most up-to-date form, for example on a display facility such as a screen or the like. Rapid changes within an object can also be contemporaneously recorded and followed on the display facility. New options, for using three-dimensional monitoring imaging for example in medical interventions, are opened up.

The updating step of the three-dimensional image dataset can in such cases include the following steps: First of all the oldest projection image which is contained in the image dataset to be updated is identified. Then the contribution of the oldest projection image is removed, for example by filtering, negation (i.e. providing with a negative sign) and back projection of the oldest projection image. Then, or if necessary simultaneously, the contribution of the currently recorded projection image is inserted into the three-dimensional image dataset for example by filtering and back projection of the current projection image.

In a first alternative there can be provision for all projection images contributing to the current image dataset to be inserted with the same weighting. The window previously mentioned is thus a "binary window" which has the advantage that only the two said images, namely of the oldest projection image contained in the three-dimensional image dataset to be updated and the current projection image have to be taken into account in the updating step. This variant is also extremely efficient in terms of processing time.

In an alternate embodiment there can be provision for the projection images being included in the current image dataset to be included weighted in accordance with the time at which they were recorded, with older projection images having a lower weighting than newer projection images or a predetermined number of the oldest and newest projection images having a lower weighting and after each recording of a current projection image the proportion of those images contributing to the image dataset of which the weighting has changed to be partly removed from the image dataset depending on the reduction in the weighting. In this case a non-binary window is thus provided with which the contributions of the older projections to the 3D image dataset are weighted lower than the contributions of the more current projections. Although this case is somewhat more complex in terms of processing since all projection images which are affected by the change in weighting must be handled in an updating step and not only the oldest and the current projection image, in this variant however old content is suppressed so that a greater focus can be placed on the more up-to-date contents. In order to still make possible updating that is efficient in computing terms there can be provision for only a specific number of the oldest images, especially the three to five oldest images, to be given a weighting other than one. Then only the specific number of the oldest projection images must additionally be taken into account. Ultimately there is thus a broad plateau of a weighting of 1. In particular in the case in which the different recording geometries are accessed sequentially or at least in a predetermined sequence and in which more images than recording geometries are taken into account for reconstruction it can be sensible for a prespecified number of the oldest and prespecified number of the newest projection images to be given a lower weighting since this simultaneously prevents specific projection directions, i.e. recording geometries, from contributing too greatly. In this case it is especially expedient for the newer images of a recording geometry to be more heavily weighted than the old images of a recording geometry. For example there can be provision for the current projection images of a recording geometry recorded to be included with the weighting factor of 0.8, but for the corresponding old images to be included with the weighting factor of 0.2 or the like.

The different recording geometries can be used sequentially along a scanning trajectory for recording a projection image or a stochastic consecutive use of the recording geometries to record a projection image can be undertaken. Whereas in commercially available systems which attempt to follow the scanning track by means of mechanical means, for example a rotatable C-arm or the like, a sequential processing of the consecutive recording geometries based on the shortest movement times between the different recordings could be more advantageous, the inventive method however also allows a stochastic or pseudo-stochastic interconnection of the recording geometries. Especially advantageously a stochastic use of the recording geometries is able to be used however in the following more closely discussed case of the so-called distributed X-ray emitter which comprises a number of spatially differently arranged X-ray sources which will be examined in greater detail in the concrete forms of embodiment of the inventive method.

In an especially advantageous embodiment of the present invention, especially with stochastic usage of the recording geometries, an X-ray emitter comprising a number of spatially differently arranged X-ray sources can be used to record the projection images, especially an X-ray emitter comprising carbon nanotubes. In this case the emitter also typically comprises individual X-ray sources arranged as an array or matrix which consequently (with the recording device at a standstill mechanically) all define separate recording geometries. Since for example distributed X-ray emitters are known which cover 10-15° as an angle interval, it is conceivable in suitable applications without a mechanical movement to operate solely with the interconnection of the different X-ray sources. This is thus advantageous simply because the time for switching over between the different X-ray sources is shorter than the time which would be needed for a mechanical movement. On the other hand such a procedure, in an especially advantageous manner, as already indicated above, allows a stochastic interconnection of the different recording geometries at high speed so that this type of stochastic switching is especially suitable for the case in which the first number is smaller than the number of recording geometries available, since then a greater coverage of the overall angle interval which is covered by the recording geometries is achieved for the individual three-dimensional image datasets.

While distributed X-ray emitters are known which consist of a number of X-ray tubes or the like disposed alongside one another, it is especially advantageous to use an X-ray emitter which uses a number of carbon nanotubes (CNT). These are especially well suited as emission cathodes since even at a small operating power they can emit a focused, strong electron beam which is then for example able to be assigned to a focusing point which is assigned to one of the driven carbon nanotubes on a long anode, especially a static anode. By operating the different carbon nanotubes different recording geometries can then be realized on the basis of the different focal points which in the final analysis form the X-ray beam sources.

In a first variant of the invention in which the first number of projection images which contribute to the three-dimensional image dataset is smaller than the number of recording geometries, a stochastic use of the recording geometries can be undertaken especially by random permutations of the recording geometries. This has already been discussed; it has the advantage that not every recording geometry, i.e. every angular position, is used for the image dataset but it can be ensured in most cases through the stochastic scattering that the overall angle interval that the recording geometries define is largely covered. A simultaneous coverage can for example be realized by random permutations of the different recording geometries being switched one after the other. It is also conceivable to prespecify a fixed, non-sequential permutation of the recording geometries right from the start. Especially advantageously such an approach, as already mentioned, can be realized if a distributed X-ray emitter is used. The selection of the first number influences the trade-off between image quality and time resolution since a smaller first number would deliver a more strongly artifact-prone reconstruction but also, within the time needed for running through all recording geometries, can deliver a number of completely independent reconstructions.

A second variant of the inventive method especially efficient in processing terms can be used if the first figure corresponds to the number of recording geometries and the recording geometries are used in a way such that after the first number of recordings the same recording geometry is used again. There can then be provision, after each recording of a current projection image, for a differential image to first be recorded from the current projection image and the oldest projection image contained in the image dataset recorded in the same recording geometry, which differential image is then back projected. Regardless of the (fixed) permutation in which the recording geometries are used, a projection showing the object from the same projection angle is always present after the first number of projection images, so that the updating of the image dataset can be undertaken even more efficiently by a differential image being considered consequently only a filtering and back projection, namely of this differential image is needed.

A third variant of the present invention relates to the case in which the first figure exceeds the number of recording geometries. There can then be provision for a redundant weighting to be used for recording geometries needed a number of times. The interconnection of the different recording geometries can be sequential or stochastic in this case. A window width selected in such a way makes it possible to average the three-dimensional image dataset over time, with the reconstruction, as described, being undertaken with due regard to possible data redundancies. The corresponding algorithms are known from the state of the art. Such a procedure with a large first number can for example be applied to the use of carbon nanotubes which exhibit a low power and thus the high noise in the projection images. It is then sensible to undertake an averaging over a longer range.

In a further expedient embodiment of the present invention there can be general provision that, after a predefined number of updates of the image dataset on the basis of the currently recorded projection image, a complete new reconstruction is undertaken. In this way accumulated errors, for example rounding errors of the processing device/control device used can be avoided during the updating steps by a complete reconstruction being undertaken again after a certain time.

In accordance with the method the invention also relates to an X-ray device comprising a control device embodied for carrying out the inventive method. All the embodiments in relation to the inventive method can be transferred similarly to the inventive X-ray device with which consequently the advantage of a contemporaneous, rapid three-dimensional supervision is likewise achieved.

In this case there can especially be provision for the X-ray device to comprise an X-ray emitter comprising a number of spatially differently arranged X-ray sources, especially an X-ray emitter comprising carbon nanotubes. The advantages produced in this case have already been described in detail in relation to the method.

BRIEF DESCRIPTION OF THE DRAWINGS

Further advantages and details of the present invention emerge from the exemplary embodiment described below as well as with reference to the drawing, in which.

DETAILED DESCRIPTION OF THE INVENTION

Figure 1:
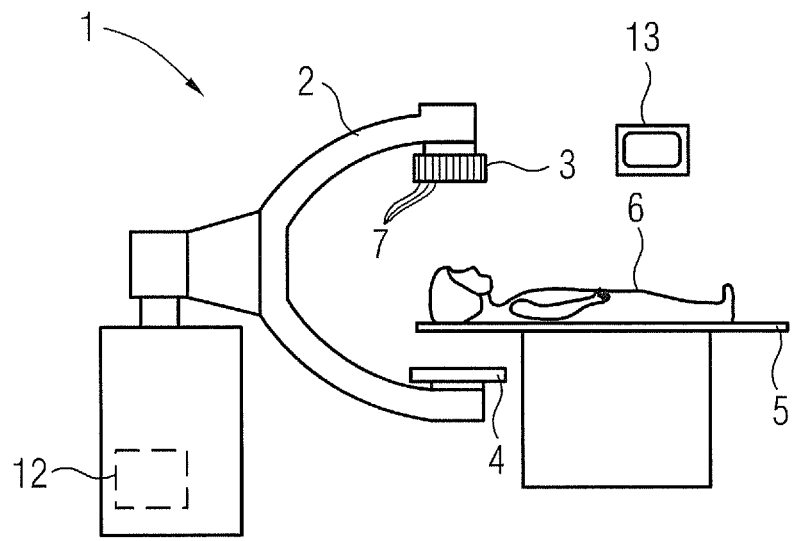
FIG. 1 shows an inventive X-ray device.

FIG. 1 shows an inventive X-ray device 1. It comprises a C-arm 2 with an X-ray emitter 3 and an X-ray detector 4 which are arranged opposite one another at ends of the C-arm 2. The C-arm 2 can be rotated around a patient 6 arranged on a patient table 5 in order to record different projection images from different projection angles, i.e. with different recording geometries.

In addition the X-ray emitter 3 involves the so-called distributed X-ray emitter which means that it has a number of individual X-ray sources 7 which each also define different recording geometries.

Figure 2:
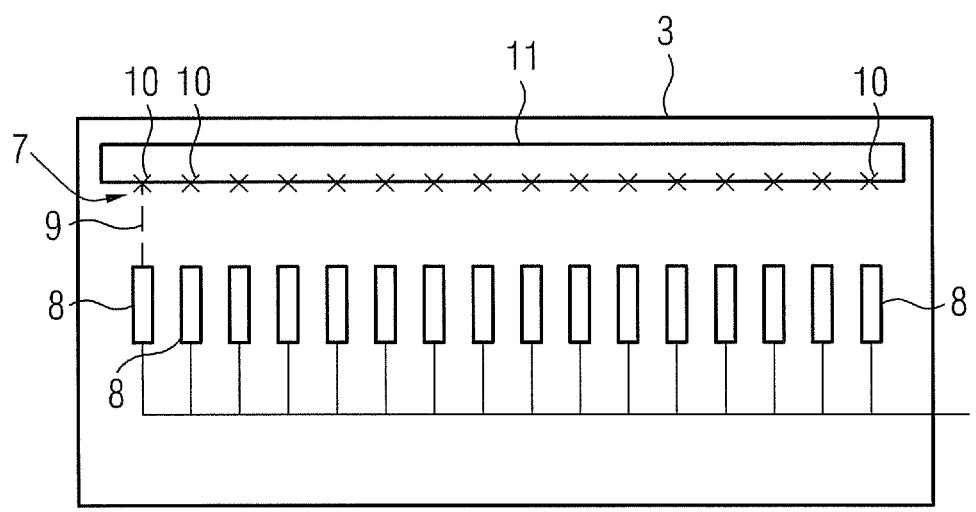
FIG. 2 shows a basic diagram of the X-ray emitter of the X-ray device.

The X-ray emitter 3 is explained in greater detail by the basic diagram of FIG. 2. It can be seen from this diagram that the X-ray emitter 3 comprises a number of carbon nanotubes 8 which are able to be operated selectively as emission cathodes. If a carbon nanotube 8 is operated, it directs an electron beam 9 onto a focal point 10 of a long fixed anode 11 assigned to it. Each of the focal points 10 thus acts in the final analysis as an X-ray source 7.

Such an X-ray emitter 3 can for example have a width of 30 cm and an angle interval of 10-15 degrees. It should be pointed out at this juncture that the inventive method can basically be executed with a standard non-distributed X-ray emitter with only one single X-ray source.

For control the X-ray device 1 also comprises a control device 12 which is embodied for carrying out the inventive method. This means that it is not only able to reconstruct three-dimensional image datasets from two-dimensional X-ray projection images which have been recorded at different projection angles, i.e. with different recording geometries, here by means of a back projection method, but that also after each recording of a current projection image the proportion of the oldest projection image contained in the current three-dimensional image dataset is removed from the three-dimensional image datasets and the proportion of the current projection image is inserted. Contemporaneously the control device 12 can thus determine an updated three-dimensional image dataset which can then be displayed on the display facility 13, here a screen, for example so that a doctor or the like can also undertake three-dimensional monitoring during a medical intervention. Naturally one or more representations derived from the three-dimensional image dataset can be generated and displayed.

Two variants of the inventive method are now explained which refer back to FIGS. 3 and 4.

Figure 3:
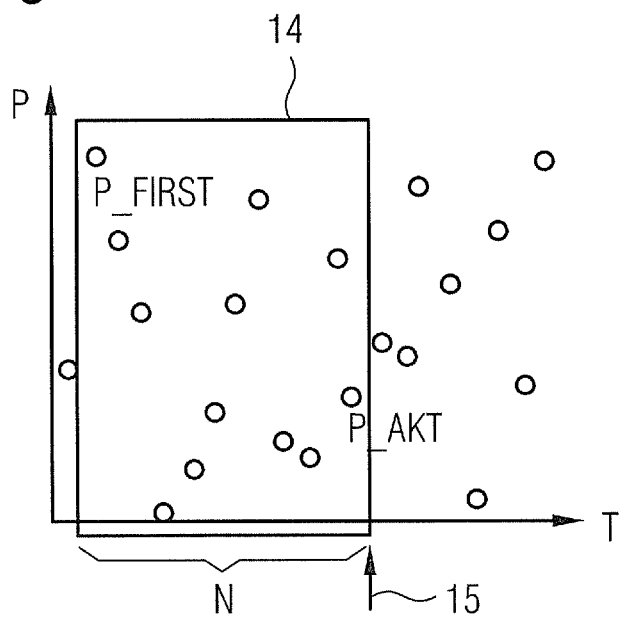
FIG. 3 shows a first diagram for recording and evaluating projection images.

FIG. 3 relates to a case in which the first number N of projection images being included in the three-dimensional image dataset respectively is smaller than the total number N_TOT of recording geometries available. The recording geometries P are plotted schematically against the recording time T. In the example in accordance with FIG. 3 a stochastic usage of the recording geometries is used, which means the recording geometries are not moved sequentially on the basis of a (virtual) sampling track but use is made of the fact that, because of the distributed X-ray emitter 3, it is easy and quick to switch between the different recording geometries. Thus, despite projection images of all recording geometries not being able to be included in the image dataset, a good coverage is made possible because of the stochastic movement. In this case available stochastically-changed permutations are used to ensure that an even distribution of the recording geometries is available.

The N projection images which are included in the current three-dimensional image dataset thus lie in the present example in a sliding, binary window 14 which ends at the current point in time 15.

Whenever a new projection image has been recorded, in FIG. 3 for example the current projection image P_AKT, the three-dimensional image dataset is updated. This means the following sequence of steps.

At the beginning the image which is the oldest image contributing to the image dataset is determined. In the example depicted in FIG. 3 this involves the projection image P_FIRST, which is then first filtered and is provided with a negative leading sign. The "negative" image created in this way is extracted from the image dataset again by a normal back projection process, meaning that the proportions of the oldest projection image P_FIRST are removed from the image dataset. Then the actual projection image P_AKT is filtered and back projected, consequently inserted into the three-dimensional image dataset.

Thus only two back projections have to be computed for the use of a binary window, which allows an efficient updating of the image dataset. The updated three-dimensional image dataset or the representation derived therefrom are then displayed on the display facility 13.

Figure 4:
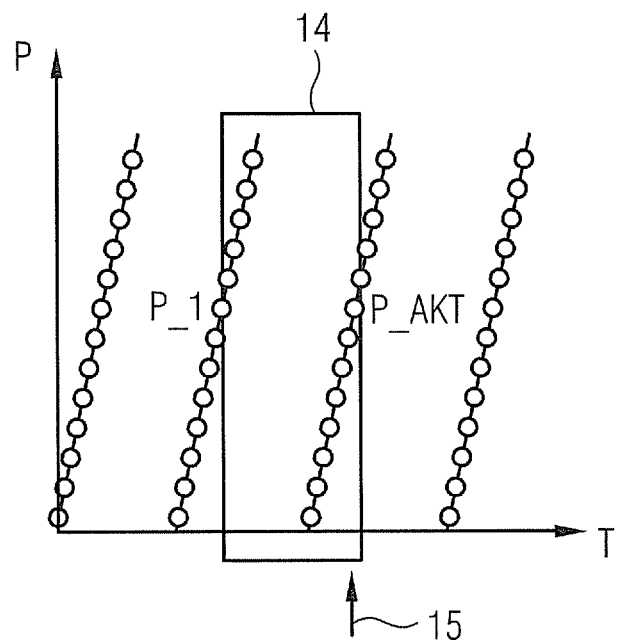
FIG. 4 shows a second diagram for recording and evaluating projection images.

FIG. 4 shows another variant of the inventive method. In this method there is provision for the projection images to be recorded by sequentially running through the recording geometries, as can be seen from FIG. 4. On the other hand precisely as many projection images N contribute to the image dataset as there are existing recording geometries, in other words the first number N corresponds to the number N_TOT of the recording geometries. In this way it is ensured that, for a newly recorded projection image P_AKT, the oldest projection image P_1 contained in the image dataset to be updated has been recorded in the same recording geometry. The removal of the components of P_1 and the insertion of the components of the current projection image P_AKT can then be undertaken elegantly using only a single filtering and back projection, in that initially a differential image P_AKT−P_1 is computed. This differential image can then be filtered in a similar way to the filter step of the algorithm of the filtered back projection used, after which the back projection of the filtered differential image is undertaken. This is also done like the back projection step of the algorithm of the filtered back projection used. An even faster computation in the updating step is thus possible.

It should finally be noted that, in the event of the first number N being greater than N_TOT, it is possible to proceed as described in relation to FIG. 3, with however possible data redundancies having to be taken into account.

To avoid accumulating errors during the updating steps, in the exemplary embodiments described there is also provision that after a certain time, ultimately after a prespecified number of updating steps, a complete, entirely new reconstructed image dataset is defined which is then subsequently updated again as normal.

In conclusion it should be stated that instead of the shown and described binary window 14, non-binary windows can also be used to select the last N projection images.

In this case a window is conceivable with which the contributions of the older projections to the three-dimensional image dataset are given a lower weighting than the contributions of the more recent projection images. In a practical exemplary embodiment for example the three oldest projection images could be given lower weightings than the rest of the projection images. In this case however the updating step should be expanded such that not only the oldest and the current projection image are processed but that also all projection images are taken into account which are affected by a change in their weighting. Windows with a broad plateau of weighting 1 are thus recommended.

The invention claimed is:

1. A method for reconstructing a three-dimensional image dataset of an object during a monitoring process, comprising:
   continuously recording two-dimensional X-ray projection images of the object from different projection angles corresponding to different recording geometries at a recording frequency;
   reconstructing the three-dimensional image dataset after recording a first number of the projection images by back projection the first number of the projection images; and
   removing a contribution of an oldest recorded two-dimensional projection image from the three-dimensional image dataset after each recoding of a current projection image; and
   updating the three-dimensional image dataset by inserting a contribution of the currently recorded projection image in the three-dimensional image dataset by back projection of the currently recorded projection image so that the three-dimensional image dataset is updated at a same frequency with the recoding frequency.

2. The method as claimed in claim 1, wherein the projection images contributing to the three-dimensional image dataset comprise a same weighting.

3. The method as claimed in claim 1, wherein the projection images contributing to the three-dimensional image dataset are weighted based on recording times.

4. The method as claimed in claim 3,
   wherein older projection images or a predetermined number of projection images comprise a lower weighting, and
   wherein the older projection images or the predetermined number of projection images having the lower weighting are partially removed from the three-dimensional image dataset after each recording of the current projection image.

5. The method as claimed in claim 4, wherein a specific number of the older projection images comprise the weighting that is other than one.

6. The method as claimed in claim 5, wherein the specific number of the older projection images is three to five.

7. The method as claimed in claim 1, wherein the different recording geometries are sequential along a sampling trajectory or stochastic for recording the projection images.

8. The method as claimed in claim 7, wherein the stochastic different recording geometries are used for recording the projection images by an X-ray emitter comprising a number of spatially differently arranged X-ray sources.

9. The method as claimed in claim 8, wherein the X-ray emitter comprises carbon nanotubes.

10. The method as claimed in claim 7, wherein the stochastic different recording geometries are used for recording the first number of the project images that is smaller than a number of the different recording geometries.

11. The method as claimed in claim 10, wherein the stochastic different recording geometries are randomly permutated.

12. The method as claimed in claim 10,
    wherein same recording geometries are used again after recording the first number of the projection images,
    wherein a differential image is formed from the current recorded projection image and the oldest projection image in the three-dimensional image dataset recorded with a same projection geometry after each recording of the current projection image, and
    wherein the differential image is back projected.

13. The method as claimed in claim 1, wherein a redundancy weighting is used for multiple-used recording geometries if the first number of projection images exceeds a number of the different recording geometries.

14. The method as claimed in claim 1, wherein a complete previously presented three-dimensional image dataset is reconstructed after a predetermined number of updates of the three-dimensional image dataset based on the currently recorded projection image.

15. The method as claimed in claim 1, wherein the three-dimensional image dataset is reconstructed by a back projection method.

16. An X-ray device, comprising:
    an X-ray emitter that emits X-ray;
    an X-ray detector that continuously records two-dimensional X-ray projection images of the object from different projection angles corresponding to different recording geometries at a recording frequency; and a control device that:
reconstructs the three-dimensional image dataset after recording a first number of the projection images by back projection the first number of the projection images; and removes a contribution of an oldest recorded two-dimensional projection image from the three-dimensional image dataset after each recoding of a current projection image; and updating the three-dimensional image dataset by inserting a contribution of the currently recorded projection image in the three-dimensional image dataset by back projection of the currently recorded projection image so that the three-dimensional image dataset is updated at a same frequency with the recoding frequency.

17. The X-ray device as claimed in claim 16, wherein the X-ray emitter comprising a number of spatially differently arranged X-ray sources.

18. The X-ray device as claimed in claim 16, wherein the X-ray emitter comprises carbon nanotubes.

19. The method as claimed in claim 1, wherein the contribution of the oldest recorded two-dimensional projection image is removed from the three-dimensional image dataset by providing a negative leading sign.

20. The method as claimed in claim 1, wherein the contribution of the currently recorded projection image is inserted in the three-dimensional image dataset simultaneously when removing the contribution of the oldest recorded two-dimensional projection image from the three-dimensional image dataset.

* * * * *